United States Patent [19]

Nagaraja et al.

[11] Patent Number: 5,861,162
[45] Date of Patent: Jan. 19, 1999

[54] MULTIVALENT INOCULA FOR LESSENING INCIDENCE OF LIVER ABSCESSES IN CATTLE

[75] Inventors: Tiruvoor G. Nagaraja; Muckatira M. Chengappa, both of Manhattan, Kans.

[73] Assignee: Kansas State University Research Foundation, Manhattan, Kans.

[21] Appl. No.: 483,382

[22] Filed: Jun. 7, 1995

[51] Int. Cl.⁶ .................. A61K 39/116; A61K 39/05; A61K 39/02
[52] U.S. Cl. ................... 424/203.1; 424/238.1; 424/234.1
[58] Field of Search .............. 424/203.1, 238.1, 424/234.1

[56] References Cited

U.S. PATENT DOCUMENTS

| | | | |
|---|---|---|---|
| 3,853,990 | 12/1974 | Madigan et al. | 424/87 |
| 4,167,560 | 9/1979 | Wohler, Jr. | 424/90 |
| 4,374,827 | 2/1983 | Sindo et al. | 424/92 |
| 4,756,907 | 7/1988 | Beck et al. | 424/85 |
| 4,919,929 | 4/1990 | Beck | 424/88 |
| 5,198,215 | 3/1993 | De Cueninck | 424/92 |

FOREIGN PATENT DOCUMENTS

| | | | |
|---|---|---|---|
| 0460480 | 12/1991 | European Pat. Off. | A61K 35/74 |
| 9400556 | 1/1994 | WIPO | C12N 1/100 |

OTHER PUBLICATIONS

Smith et al.; Further Observations on Enhancement of the Infectivity of *Fusobacterium necrophorum* by other bacteria; Epidemiol. Infext. (1991), 106:305–310, Month Not Available.

Smith et al.; Enhancement of the Infectivity of *Fusobacterium necrophorum* by other bacteria; Epidem. Inf. (1989), 102:447–458, Month Not Available.

Roberts; The pathogenic Synergy of Fusiformis Necrophorus and Corynebacterium Pyogenes; Brt. J. of Exp. Pathology, (1967), 48:674–679, Month Not Available.

Roberts et al.; Infective Bulbar Necrosis (Heel–Abscess) of Sheep, a Mixed Infection with *Fusiformis Necrophorus and Corynecbacterium Pyogenes*, J. Comp. Path. (1967), 78:1–9, Month Not Available.

Roberts; The pathogenic Synergy of *Fusiformis Necrophorus*and *Corynebacterium Pyogenes*; Brt. J. of Exp. Pathology, (1967), 48:665–673, Month Not Available.

Takeuchi, et al.; O/Pathogenic Synergism of *Fusobacterium necrophorum* and Other Bacteria in Formation of Liver Abscess in BALB/c Mice, Jpn. J. Vet. Sci., 45(6), 775–781 (1983), Month Not Available.

Langworth, B.F., *Fusobacterium necrophorum,*Bacteriol. Rev. (1977), 41:373–390.

Lechtenberg, et al.; Bacteriologic and histologic studies of hepatic abscesses in cattle; Am. J. Vet. Res., (1988), 49:58–62, Month Not Available.

Nagaraja et al.; Susceptibility and resistance of ruminal bacteria to antimicrobial feed additives; Appl. Environ. Microbiol., (1987), 53:1620–1625, Month Not Available.

Potter et al.; Effect of monensin and tylosin on average daily gain, feed efficiency and liver abscess incidence in feedlot cattle; J. Anim. Sci. (1985), 61:1058–1065, Month Not Available.

Scanlan, et al.; Bovine rumenitis–liver abscess complex: a bacteriologial review; Cornell Vet. (1983), 73:288–297, Month Not Available.

Smith, H.A., Ulcerative lesions of the bovine rumen and their possible relation to hepatic abscesses; (1994); Am. J. Vet. Res.; 5:234–242, Month Not Available.

Tan et al.; Factors affecting the leukotoxin activity of *Fusobacterium necrophorum;* Vet. Microbiol., (1992); 32:15–18, Month Not Available.

Tan et al.; Serum neutralizing antibodies against *Fusobacterium necrophorum* leukotoxin in cattle with experimentally induced or naturally developed hepatic abscesses: (1994a); J. Anim. Sci., 72:502–508, Month Not Available.

Emery et al.; Biochemical and functional properties of a leucocidin produced by several strains of *Fusobacterium necrophorum;*(1984); Aus. Vet. J.; 61:382–385, Month Not Available.

Scanlan et al.; Biochemical characterization of the leukotoxins of three bovine strains of *Fusobacterium necrophorum;* Am. J. Vet Res.; (1986); 47:1422–1425, Month Not Available.

Garcia; et al.; Results of a Preliminary Trial with *Sphaerophrous necrophorus*Toxoids to Control Liver Abscesses in Feedlot Cattle; Can. J. Comp. Med., (1974); 38:222–226, Month Not Available.

Abe et al.; *Fusobacterium necrophorum* Mice as a Model for the Study of Liver Abscess Formation and Induction of Immunity; Infection and Immunity (1976); 13:1473–1478, Month Not Available.

(List continued on next page.)

Primary Examiner—Louise N. Leary
Attorney, Agent, or Firm—Hovey, Williams, Timmons & Collins

[57] ABSTRACT

Novel inocula for administration to ruminant animals such as cattle or sheep are provided in order to immunize the animals and lessen the incidence of liver abscesses and/or foot rot therein. In one aspect, the invention pertains to an *A. pyogenes*-derived vaccine including an inactivated cell culture product (e.g., cell-elaborated supernatant) from *A. pyogenes* cell culture in a suitable carrier. In another aspect, the invention relates to a multivalent vaccine including at least first and second bacterial components in a carrier; the first component comprises an inactivated cell culture product of *A. pyogenes* whereas the second component comprises an inactivated cell culture product of *F. necrophorum*. The inocula of the present invention find particular utility in incidences where ruminant animals are particularly subject to *A. pyogenes* infection leading to liver abscesses and/or foot rot, e.g., where the animals are regularly treated with an antibiotic or where cattle are fed a high grain content concentrate diet.

2 Claims, No Drawings

OTHER PUBLICATIONS

Garcia et al.; Biological Characterization of *Fusobacterium necrophorum* Cell Fractions in Preparation for Toxin and Immunization Studies; Infect. Immun.; (1975); 11:609–616, Month Not Available.

Warner et al.; Passive Hemmagglutination Test for Determining the Immune Response of Rabbits to *Sphaerophorus necrophorus* of Bovine Hepatic Abscess Origin; Am. J. Vet. Res.; (1974); 35:551–554, Month Not Available.

Coyle–Dennis, et al.; Biological and Biochemical Characteristics of *Fusobacterium necrophorum* Leukocidin; Am. J. Vet Res. (1978); 39:1790–1793, Month Not Available.

Emery et al.; Generation of Immunity Against *Fusobacterium necrophorum* in Mice Inoculated with Extracts Containing Leucocidin; Veterinary Microbiology; (1986); 12:255–268, Month Not Available.

Watts et al.; Evaluation of a Rapid Inoculum Standardization System for Antimicrobial Susceptibility Testing of Bacterial Isolates From the Bovine Mammary Gland;, Month Not Available.

Emery et al.; Studies on the Purification of the Leucocidin of *Fusibacteriun Necrophorum* and its Neutralization by Specific Antisera; Veterinary Microbiology, 11 (1986);357–372, Month Not Available.

Cameron et al.; Failure to inducein rabbits effective pyogenes with a combined bacterin; Onderstepoort J. Vet. Res. 44 (4), 253–256 (1977), Month Not Available.

MULTIVALENT INOCULA FOR LESSENING INCIDENCE OF LIVER ABSCESSES IN CATTLE

BACKGROUND OF THE INVENTION

1. Field of the Invention

The present invention is broadly concerned with novel inocula for administration to cattle or sheep in order to lessen or prevent the incidence of liver abscesses and/or foot rot. More particularly, the invention pertains to such inocula, methods of preparing the same and methods of lessening the incidence of liver abscesses and/or foot rot in cattle or sheep via administration of the inocula. In one aspect, the invention relates to an *A. pyogenes*-derived inoculum, and in another aspect to a multivalent inoculum comprising a first bacterial component in the form of an inactivated cell culture product of *A. pyogenes* and a second bacterial component in the form of an inactivated cell culture product of *F. necrophorum*.

2. Description of the Prior Art

Liver abscesses in feed lot cattle are a serious economic problem, causing condemnation of over 3 million livers and an estimated loss of $15 million annually in the United States. This estimate is based primarily on condemnation of liver and other organs, and does not include economic losses stemming from reduced feed efficiencies and lowered weight gains. A number of studies have confirmed that cattle with abscessed livers gain less (average 4–5%) and have reduced feed efficiencies (average 7%) compared with cattle having healthy livers. The average incidence of abscessed liver in grain-fed cattle approximates 25–30%.

Liver abscesses in cattle are part of a disease complex where the abscessation is secondary to primary foci of infection in the rumen epithelium. The pathogenesis can be summarized as follows: (1) ruminal lesions are induced by acidosis that follows rapid change in diet from high-roughage to high grain, prolonged feeding of high grain diet (sometimes referred to as an all-concentrate diet), or occasionally by foreign body penetration of the rumen epithelium; (2) bacteria present in the rumen invade the epithelium and form focal abscesses in the rumen wall; and (3) bacteria enter the portal circulation, and are carried to the liver where they localize in the parenchyma with subsequent abscess formation.

*F. necrophorum* is the primary etiologic agent of liver abscesses in ruminant animals. The organism has been recognized as an animal and human pathogen since the late 1800s, and is associated with numerous necrotic disease conditions in domestic and wild animals. In addition to liver abscesses, the organism is also the primary etiologic agent of foot rot, foot abscesses, calf diphtheria, and is frequently isolated from cases of mastitis, metritis, and necrotic lesions of the oral cavity.

The ability of *F. necrophorum* to establish in the liver is attributed to the production of a toxin called leukotoxin (or leucocidin). The toxin is soluble, proteinaceous and has specificity for bovine leukocytes. The leukotoxin is believed to aid in the establishment of *F. necrophorum* in the liver by directly impairing the normal defense mechanism and indirectly by the damage caused by cytolytic products released from neutrophils and macrophages to the hepatic cells. Therefore, the leukotoxin elaborated from *F. necrophorum* plays a critical role in *F. necrophorum* infection of the liver.

*F. necrophorum* is a gram-negative, nonsporeforming, nonmotile, strictly anaerobic and pleomorphic organism. Morphologically, the organism varies from short rods to filamentous with pointed and rounded ends. Cell lengths range from coracoid bodies of 0.5–0.7 μm in diameter to filaments over 100 μm. Surface colonies are 1–2 mm in diameter, circular, transparent to opaque, and with some strains producing α or β hemolysis. The organism ferments glucose, fructose and maltose only weakly with final pH around 5.0–6.3. It ferments lactate to acetate, propionate, and butyrate. Butyrate is the major product from lactate fermentation. Indole is produced from peptone. *F. necrophorum* has been isolated from the normal flora in the oral cavity, gastrointestinal cavity, and genitourinary tract of humans and animals. The organism is also known to survive in the soil.

Four biotypes (A, B, AB and C) of *F. necrophorum* have been described. Biotype A, most frequently isolated from liver abscesses, is more pathogenic than biotype B, which predominates in ruminal wall abscesses. Biotype AB is rarely isolated, and has pathogenicity intermediate that of biotypes A and B. Biotype C is non-pathogenic.

It has been suggested in the past to utilize *F. necrophorum* bacterin as an agent for immunizing cattle and sheep against liver necrosis, EPO Application No. 460480 of Dec. 11, 1991. Specifically, virulent *F. necrophorum* isolates are inactivated using β-propiolactone, followed by addition of adjuvants. In addition, Abe et al. (*Infection and Immunity*, 13:1473–1478, 1976) grew *F. necrophorum* for 48 hours. Cells were obtained by centrifuging, washing three times with saline, and were inactivated with formalin (0.4% in saline). The inactivated cells were then injected into mice to induce immunity. Two weeks after the last booster injection, each mouse was challenged with viable cells of *F. necrophorum*. The mice immunized with killed cells and challenged with live cells had no detectable bacteria in the liver, lung or spleen for up to 28 days. It was concluded that immunization of mice with formalin-killed *F. necrophorum* conferred protection against infection. Garcia et al. (*Canadian J. Comp. Med*, 38:222–226, 1974) conducted field trials to evaluate the efficacy of alum-precipitated toxoids of *F. necrophorum*. The vaccine preparation consisted of washed cells (unlikely to contain leukotoxin) that were ruptured by sonication. The most promising result was achieved with the injection of 15.5 mg protein of cytoplasmic toxoid. In this group, the incidents of liver abscesses was reduced to 10% from an average 35% in the control group. Finally, Emery et al., (*Vet. Microbiol.*, 12:255–268, 1986) prepared material by gel filtration of 18-hour culture supernate of *F. necrophorum*. This elicited significant immunity against challenged from viable *F. necrophorum*. The injected preparation contained endotoxin and the majority of the leukotoxic activity.

PCT Publication WO 94/00556 published Jan. 6, 1994 describes novel *F. necrophorum* leukotoxid vaccines as well as methods of enhancing the elaboration of leukotoxin from *F. necrophorum* and of producing a leukotoxin vaccine. In particular, this publication discloses that *F. necrophorum* bacteria are advantageously cultured in growth media at a temperature of from about 35°–41° C. and a pH of from about 6.5–8 for a period of from about 4–10 hours in order to maximize the production of leukotoxin. Thereafter, culturing is terminated and the leukotoxin-bearing supernate is separated and inactivated to form a vaccine.

*Actinomyces pyogenes* is a gram-positive, cocco-bacillary shaped, facultative organism that is associated with a number of pyogenic conditions (termed "Pyobacillosis") in animals and humans. It is frequently isolated in mixed culture with other bacteria including *F. necrophorum*. In liver abscesses and foot rot in cattle, *A. pyogenes* is the second most frequent pathogen isolated. In addition to liver abscesses and foot rot, the organism is also a frequent isolated from pyogenic infections of a number of organs such as lungs, mammary glands, joints and the uterus. The pathogenic mechanism of *A. pyogenes* is not well understood. Some of the factors that contribute to pathogenicity include exotoxins (hemolysin or leukotoxin) and enzymes such as proteinase, DNases, and neuraminidase. There is also evidence that *A. pyogenes* in cattle synergistically interacts with other bacteria including *F. necrophorum* and the combination may be more virulent than individual species. However, no *A. pyogenes*-derived vaccines or inocula for immunizing cattle and sheep against liver abscesses and/or foot rot have been prepared in the past.

SUMMARY OF THE INVENTION

The present invention relates to inocula for cattle and sheep in order to immunize such ruminants and lessen the incidence therein of liver abscesses and/or foot rot. In addition, the invention pertains to methods of preparing such inocula and of lessening the incidence of the aforementioned pathogenic conditions in cattle and sheep.

In one aspect of the invention, an inoculum for administration to cattle or sheep is provided which comprises a bacterial component and a compatible carrier mixed with the latter. The bacterial component consists essentially of an inactivated cell culture product of *A. pyogenes*; e.g., the component is selected from the group consisting of separated *A. pyogenes* cells, *A. pyogenes* cellular subunits or fragments, the supernatant elaborated by *A. pyogenes* cells in cell culture, and mixtures thereof. The carrier may be one of a number of suitable adjuvants such as alumina hydroxide or the oil-based or metallic salt adjuvants.

The *A. pyogenes* inoculum is prepared by forming a cell culture of a strain of *A. pyogenes* in a growth media such as Brain Heart Infusion broth or RPMI 1640 media using an overnight culture with incubation at 35°–39° C. for 12–48 hours. At the end of the incubation period (most preferably after about 36 hours), a cell culture product is inactivated using formalin, β-propiolactone, heat, radiation or any other known method of inactivation. In particularly preferred forms, the entire cell culture is inactivated and chilled for two days. Thereafter, the inactivated cell culture is centrifuged and the supernatant antigenic material is recovered. As indicated previously, in alternate procedures, the entire cell culture, separate cells or cellular subunits may be used as the antigenic material. In any case, after inactivation and separation as desired, the antigenic material is mixed with a suitable adjuvant carrier.

The invention also comprehends a multi-valent inoculum for administration to cattle or sheep which includes first and second bacterial components in a compatible carrier. The first bacterial component comprises an inactivated cell culture product of *A. pyogenes* and the second component comprises an inactivated cell culture product of *F. necrophorum*. The first *A. pyogenes*-derived bacterial component is prepared as set forth above, i.e., use is made of an *A. pyogenes* inoculum in accordance with the invention. The second *F. necrophorum*-derived bacterial component is prepared in the manner described in PCT Publication No. WO 94/00556 which is incorporated by reference herein. The multi-valent inocula of the invention are characterized by the property of lessening the incidence of liver abscesses in cattle inoculated therewith to a greater extent than cattle inoculated with the individual components thereof.

In more detail, the *F. necrophorum* second bacterial component for the multi-valent vaccine is in the form of inactivated leukotoxin-containing supernatant elaborated by *F. necrophorum* cells in cell culture. Culturing of *F. necrophorum* preferably involves culturing a biotype A strain in a suitable growth medium such as Brain Heart Infusion broth at a temperature of from about 35°–41° C. and a pH of from about 6.5–8 for a period of from about 4–9 hours. The preferred strain of *F. necrophorum* has ATCC Accession No. 55329. At the end of the culturing step, leukotoxin supernatant is separated and inactivated by any known means, preferably through the use of formalin. This inactivated antigenic material can then be mixed with an appropriate adjuvant, of the same type described with reference to the *A. pyogenes* vaccine preparation.

The final multivalent inoculum in accordance with the invention is prepared by mixing the first and second bacterial components derived from the respective first and second cell cultures. Preferably, the bacterial components are present in the final multivalent inoculum at about a 1:1 (v/v) ratio.

It has been determined that the inocula of the present invention will have particular utility in those cases where *A. pyogenes* becomes a significant etiological agent. For example, it has unexpectedly been found that where cattle or sheep are regularly treated (e.g., fed) with an antibiotic which reduces the incidence of liver abscesses and/or foot rot, a high percentage of infected animals exhibit *A. pyogenes* in their abscess bacterial flora. Accordingly, where ruminant animals are subjected to a regular regime of antibiotics such as tylosin, chlortetracycline, oxytetracycline, bacitracin and mixtures thereof to reduce the incidence of liver abscesses and/or foot rot, these animals should also be treated with the inocula of the present invention. In this way, the incidence of liver abscesses and/or foot rot will be further lessened.

In addition, it is known that cattle fed a high concentrate diet including at least about 90% by weight grain characteristically have a high incidence of liver abscesses (greater than 50%). It has now been discovered that a high percentage of abscessed livers from cattle fed concentrate diets exhibit *A. pyogenes* upon bacteriological examination. Therefore, cattle fed concentrate diets can also materially benefit from treatment with the inocula of the invention.

DETAILED DESCRIPTION OF THE PREFERRED EMBODIMENT

The following examples describe the preferred techniques for the production and use of a monovalent *A. pyogenes*-derived inoculum and of a multivalent inoculum containing *A. pyogenes* and *F. necrophorum* antigenic components. It is to be understood, however, that these examples are presented by way of illustration only, and nothing therein should be taken as a limitation upon the overall scope of the invention.

EXAMPLE 1

In this example, the bacterial flora of liver abscesses from feedlot cattle fed with or without the antibiotic tylosin were examined. A total of 36 liver abscesses from tylosin-fed cattle were examined, along with 41 liver abscesses from cattle not fed tylosin. This study revealed that there was a higher incidence of *A. pyogenes* in the liver abscesses of tylosin-fed animals. Accordingly, it was deduced that in tylosin-fed animals, the role of *F. necrophorum* is lessened and *A. pyogenes* assumes a greater role than in animals not fed tylosin. The results of this study are set forth in the following table.

TABLE 1

Bacterial flora of liver abscesses in cattle fed tylosin or no tylosin

| Bacteria | Tylosin | No Tylosin |
|---|---|---|
| No. of abscesses cultured | 36 | 41 |
| F. necrophorum | 36/36 (100)[a] | 41/41 (100) |
| Subsp. necrophorum[b] (biotype A) | 18/36 (50) | 34/41 (82) |
| Subsp. funduliforme (biotype B) | 3/36 | 1/41 |
| Actinomyces pyogenes[b] | 19/36 (53) | 4/41 (100 |

[a]Numbers in parentheses are percentages
[b]Chi Square test P < .01

Although the origin of F. necrophorum found in liver abscesses is well known, the source of A. pyogenes is not understood. Because A. pyogenes is aerobic, it is not a normal inhabitant of the rumen; however, the bacterium may be a component of the epimural flora of the rumen (bacteria attached to the rumen wall). Facultative or aerobic bacteria have a better chance of surviving in anaerobic conditions by adhering to the rumen wall where extensive blood supply provides oxygen. The close proximity of the rumen wall enhances the opportunity of the bacterium to get into portal circulation and thereby enter the liver. The bacteria could remain dormant and multiply if conditions (such as entry into the liver) become conducive. The higher incidence of A. pyogenes in tylosin-fed cattle is surprising because the organism is quite sensitive to tylosin.

EXAMPLE 2

In this example, the liver abscesses of cattle fed an all-concentrate diet (100% grain) were bacteriologically examined. It is known that feedlots making use of all-concentrate diets have a high incidence of liver abscesses (greater than 50%). In this study, the livers of 24 animals were examined and it was found that 19 were abscessed. Eighteen of these abscesses were cultured and F. necrophorum was found in 12 abscesses whereas A. pyogenes was found in 17 abscesses. This data is summarized in the following Table 2.

TABLE 2

Bacterial flora of liver abscesses in cattle fed all concentrated diet

| Bacteria | Incidence | Percentage |
|---|---|---|
| No. of animals | 24 | |
| Abscessed | 19 | 79 |
| No. of abscesses cultured | 18 | |
| F. necrophorum | 12 | 67 |
| Actinomyces pyogenes | 17 | 94 |

In the basis of the tests sets forth in Examples 1 and 2, it is believed that there is a synergistic interaction between F. necrophorum and A. pyogenes in causing liver abscesses. The presence of A. pyogenes may enhance the virulence of F. necrophorum or vice-versa. Table 3 sets forth the characteristics of the respective bacteria and their interactions.

TABLE 3

| Characteristics | Fusobacterium necrophorum | Actinomyces pyogenes | Interaction |
|---|---|---|---|
| $O_2$ relationship | Anaerobic | Facultative | A. pyogenes utilizes $O_2$ to create anaerobic condition for F. necrophorum growth |
| Substrate and endproducts | Ferments lactate | Produces lactate | A. pyogenes provides substrate for F. necrophorum growth |
| Leukotoxin production | Strongly positive | Negative or weakly positive | Leukotoxin of F. necrophorum protects against phagocytosis |
| Hemolysis | Weakly positive | Strongly positive | Hemolytic activity of A. pyogenes provides iron required for F. necrophorum growth |

EXAMPLE 3

In this example, the preparation of a monovalent A. pyogenes vaccine is described, as well as the preparation of a multivalent A. pyogenes/F. necrophorum vaccine.

A. pyogenes Vaccine

A suitable strain of A. pyogenes is grown in a Brain Heart Infusion broth (DIFCO Laboratories, Detroit, Mich.) or RPMI 1640 medium (GIBCO Laboratories, Grand Island, N.Y.). The growth medium is inoculated with an overnight culture (1–5% inoculum size) of A. pyogenes and is incubated at 35°–39° C. for 12–48 hours in a 5% $CO_2$ atmosphere (a standard atmosphere could also be used). At the end of the incubation period, the culture is inactivated by adding formalin (0.3–0.4%) on a vol./vol. basis. The inactivated whole culture is chilled in an ice bath and refrigerated for one or two days. Thereafter, the inactivated cell culture is centrifuged (13,500 g for 15–30 minutes) and the supernatant antigenic material is recovered. In alternative procedures, the whole cell culture (bacterin) or cellular subunits can be used as the antigenic material.

The antigenic material is then mixed with a suitable adjuvant (e.g., aluminum hydroxide or other commercially available oil-based or metallic salt adjuvant) to complete the vaccine. The vaccine may then be conventionally administered to sheep or cattle (one or more vaccinations) to elicit antibodies in the animals and will prevent the establishment of A. pyogenes in the animal's liver or feet, or any other organs.

A. pyogenes/F. necrophorum Vaccine

The F. necrophorum leukotoxoid vaccine component is prepared by growing a F. necrophorum biotype A strain (e.g., strain 25, ATCC Accession No. 55329) in a pre-reduced (0.05% cysteine HCl) anaerobically sterilized Brain-Heart Infusion broth (DIFCO Laboratories, Detroit, Mich.) at 39° C. for 7 hours (absorbance 0.8 at 600 nm). The culture supernatant is obtained by centrifugation at 13,500 g for 30 minutes at 4° C., filtered through a 0.45 µm membrane filter (Micron Separations, Inc., Westborough, Mass.) and inactivated with 0.3% formalin. F. necrophorum leukotoxin and protein concentrations in the cell culture supernatant are assayed before and after inactivation with formalin.

The inactivated supernatant is mixed with Ribi adjuvant (premixed, sterile form from Ribi Immunochem Research, Inc., Hamilton, Mont.) or other adjuvant as described above at a level of 90% leukotoxin supernatant/10% adjuvant. The mixture is then emulsified in a homogenizer.

In order to create the multivalent vaccine, the A. pyogenes vaccine and the F. necrophorum vaccine component are mixed on a 1:1 v/v basis. The multivalent vaccine can then be conventionally administered (typically via one or more injections) to cattle or sheep.

The monovalent or multivalent vaccines of the invention may be conventionally administrated via parenteral injection or other known techniques in order to elicit the production of appropriate antibodies in the ruminant animals. Such administrations may be at one time or multiple administrations spaced over a period of time.

We claim:

1. An inoculum for administration to cattle in order to lessen the incidence of liver abscesses therein, said inoculum comprising first and second bacterial components in a compatible carrier with an adjuvant, said first bacterial component comprising a formalin-inactivated supernate elaborated by *A. pyogenes* in cell culture, and said second bacterial component comprising formalin-inactivated leukotoxin-containing supernate elaborated by a biotype A strain of *F. necrophorum* in cell culture, said inoculum characterized by the properties of lessening the incidence of liver abscesses in cattle inoculated therewith as compared with non-inoculated cattle and of lessening the incidence of liver abscesses in cattle inoculated therewith as compared with cattle inoculated with said first and second components individually.

2. The inoculum of claim 1, comprising said first and second bacterial components being present in said inoculum at about a 1:1 (v/v) ratio.

* * * * *